United States Patent
Bonde et al.

(10) Patent No.: US 10,327,804 B2
(45) Date of Patent: Jun. 25, 2019

(54) PERCUTANEOUS NEEDLE GUIDE AND METHODS OF USE

(71) Applicant: Medtronic, Inc., Minneapolis, MN (US)

(72) Inventors: Eric H. Bonde, Minnetonka, MN (US); Kevin M. Cristadoro, Minneapolis, MN (US); Yelena G. Tropsha, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 417 days.

(21) Appl. No.: 14/461,822

(22) Filed: Aug. 18, 2014

(65) Prior Publication Data

US 2015/0080736 A1    Mar. 19, 2015

Related U.S. Application Data

(62) Division of application No. 13/155,142, filed on Jun. 7, 2011, now Pat. No. 8,808,187, which is a division of application No. 11/757,516, filed on Jun. 4, 2007, now Pat. No. 7,976,469.

(51) Int. Cl.
| | | |
|---|---|---|
| *A61B 8/00* | (2006.01) | |
| *A61B 17/34* | (2006.01) | |
| *A61B 5/04* | (2006.01) | |
| *A61B 8/08* | (2006.01) | |

(52) U.S. Cl.
CPC ...... *A61B 17/3403* (2013.01); *A61B 5/04001* (2013.01); *A61B 8/0841* (2013.01); *A61B 2017/3413* (2013.01)

(58) Field of Classification Search
None
See application file for complete search history.

(56) References Cited

U.S. PATENT DOCUMENTS

| | | | | |
|---|---|---|---|---|
| 5,758,650 | A * | 6/1998 | Miller | A61B 17/3403 600/461 |
| 6,104,960 | A * | 8/2000 | Duysens | A61N 1/0551 607/117 |
| 6,475,152 | B1 * | 11/2002 | Kelly, Jr. | A61B 17/3403 600/461 |
| 7,229,450 | B1 * | 6/2007 | Chitre | A61B 5/0422 600/373 |

(Continued)

*Primary Examiner* — Jonathan Cwern
(74) *Attorney, Agent, or Firm* — Withers & Keys, LLC

(57) ABSTRACT

An indicator element of a percutaneous needle guide for a medical scanning device includes a pointer for pointing to a percutaneous needle entry site on an epidermis of a body, when the guide is attached to the device and the device is positioned over the epidermis for scanning. A user may orient and insert a needle into the entry site according to the direction of the pointer, by just viewing the pointer, without the needle being constrained by the pointer. The guide may include an adjustment mechanism for moving the indicator element with respect to the device, when the guide is attached to the device; the adjustment mechanism moves the indicator element, without changing an orientation of the pointer, in a direction approximately parallel to a plane that is approximately tangent with an apex of the device transducer surface and approximately perpendicular to a longitudinal axis of the device.

13 Claims, 10 Drawing Sheets

(56) References Cited

U.S. PATENT DOCUMENTS

| | | | |
|---|---|---|---|
| 2002/0133079 A1* | 9/2002 | Sandhu | A61B 8/0833 600/464 |
| 2003/0171670 A1* | 9/2003 | Gumb | A61B 17/3403 600/411 |
| 2007/0149977 A1* | 6/2007 | Heavener | A61B 17/1764 606/87 |

* cited by examiner

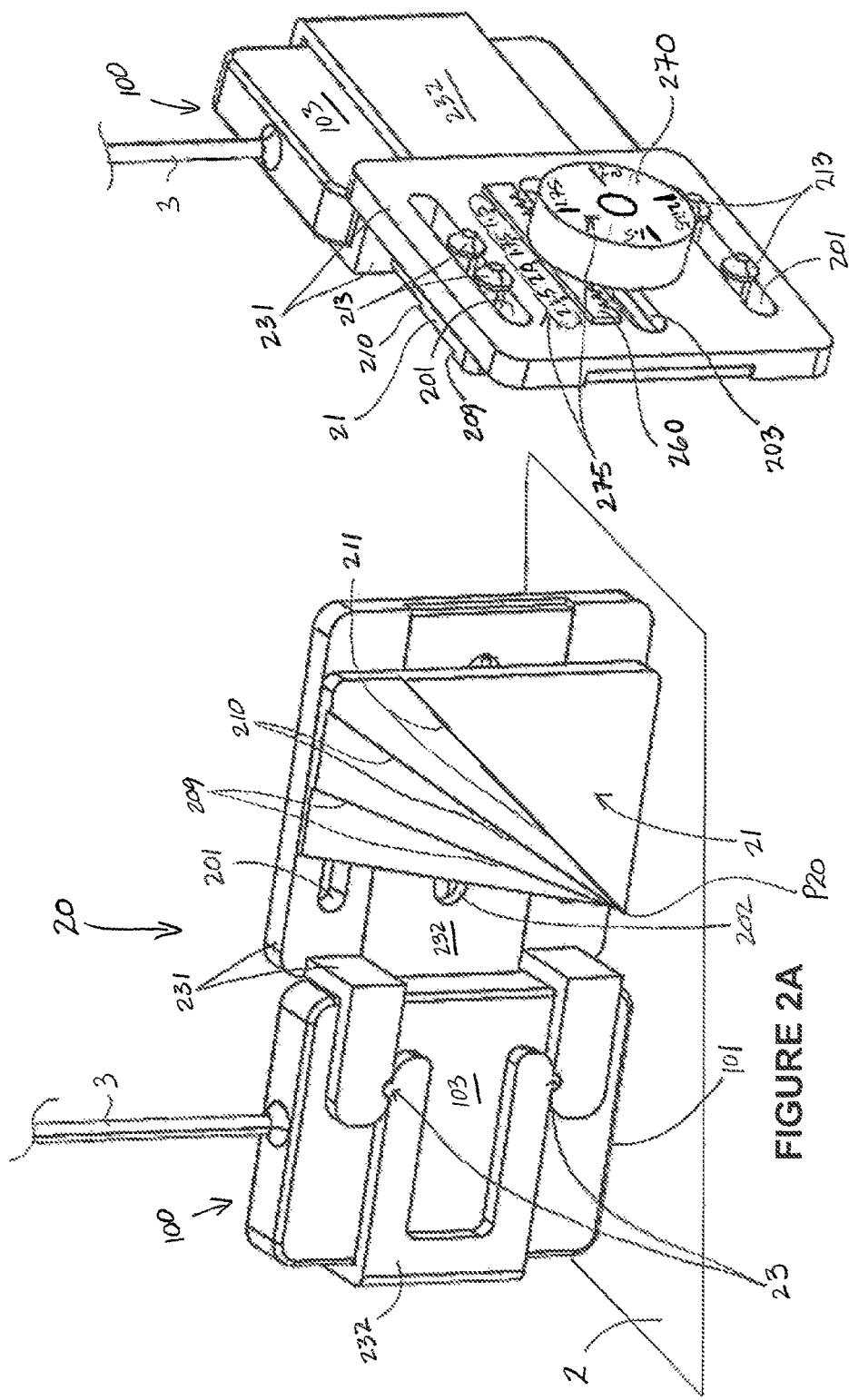

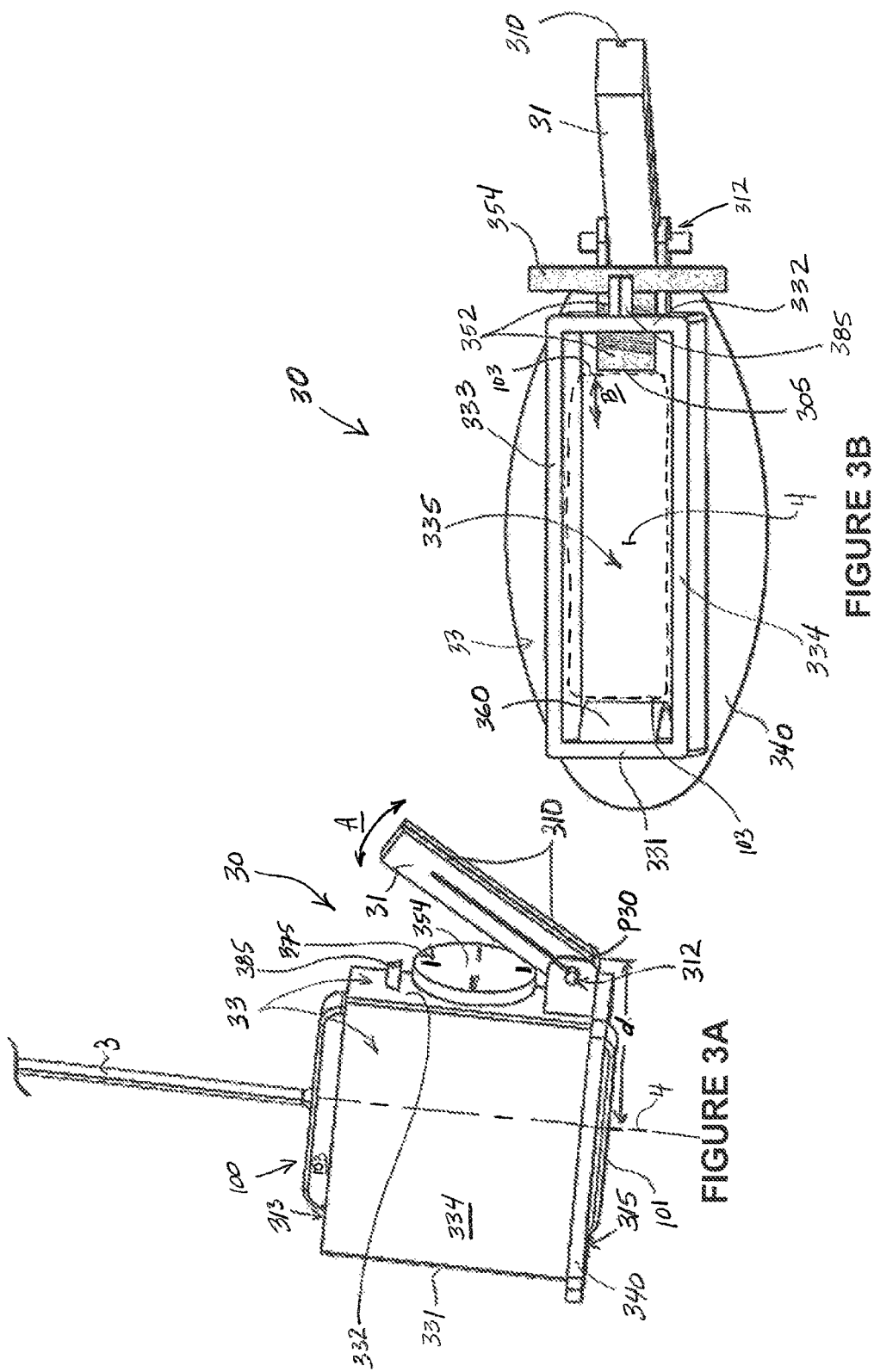

PERCUTANEOUS NEEDLE GUIDE AND METHODS OF USE

RELATED APPLICATION

This patent application is a divisional of U.S. patent application Ser. No. 11/757,516, filed Jun. 4, 2007, now allowed, the entire disclosure of which is expressly incorporated herein by reference.

TECHNICAL FIELD

The present invention pertains to gaining percutaneous access to a subcutaneous target located by a non-invasive medical scanning device and more particularly to guiding insertion of a percutaneous needle through an epidermis of a body to gain the access.

BACKGROUND

Various designs of percutaneous needle guides for attachment to non-invasive medical scanning devices, for example, hand-held ultrasound transducer probes, are known in the art. These guides may be used to direct a percutaneous needle, for example, a biopsy needle, to a needle entry site, which is located alongside the scanning device on an epidermis of a scanned body, and which corresponds to a subcutaneous target located by the device. In order to direct the needle, these guides include a constraining feature through which the needle must be passed. Many of these guides further include means to adjust an angular orientation of the constraining feature, according to a measured depth of the located target, so that the needle inserted therein is directed to the insertion site at an angle that allows the inserted needle to intersect with the subcutaneous target.

Guides which only provide for an angular adjustment of the constraining feature, in order to re-direct the trajectory of the inserted needle, do not take into account situations when a particular angular orientation of the inserted needle is important for the needle to pass through the located target and gain access to a site beyond the target. Furthermore, handling of a guide including the aforementioned constraining feature, in conjunction with a proper handling of the scanning device and the needle, can increase a number of steps that a physician or clinician must take in order to gain percutaneous access to the target or the site beyond the target. Additionally, the constraining feature through which the needle must be passed in order to be guided by these guides can impose unnecessary limitations on a physician or clinician who has developed skills for "free-hand" handling of needles.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIGS. 2A-B are first and second perspective views of a needle guide attached to a medical scanning device, according to some alternate embodiments of the present invention.

FIG. 3A is a perspective view of a needle guide attached to a medical scanning device, according to additional embodiments of the present invention.

FIG. 3B is a top perspective view of the needle guide shown in FIG. 3A, according to some embodiments.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1B:
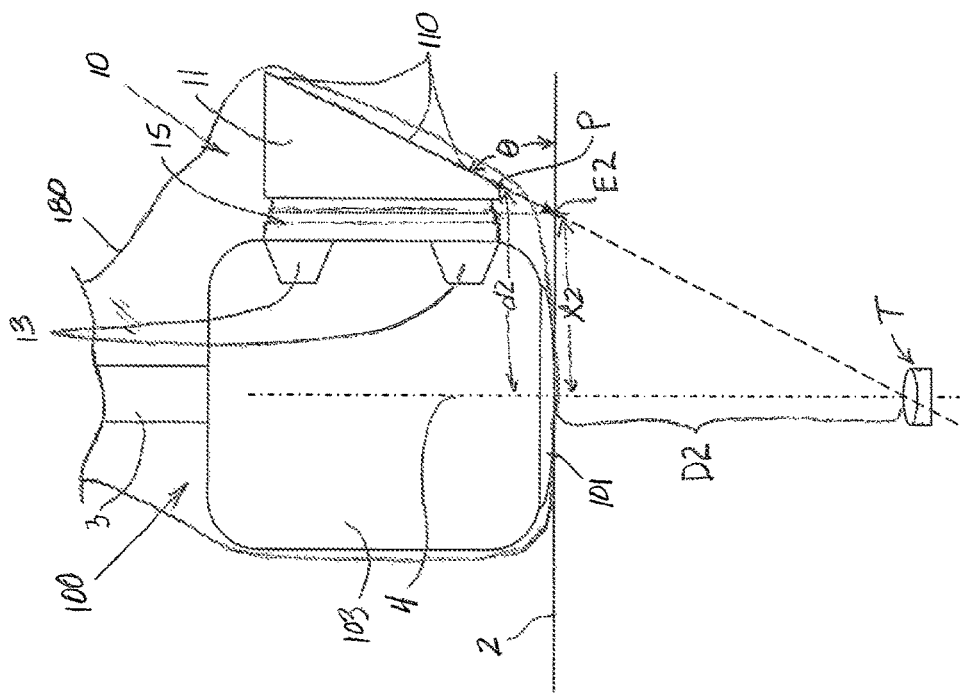
FIGS. 1A-B are schematics depicting a needle guide attached to a medical scanning device in a first position and second position, respectively, according to some embodiments of the present invention.
Figure 1A:
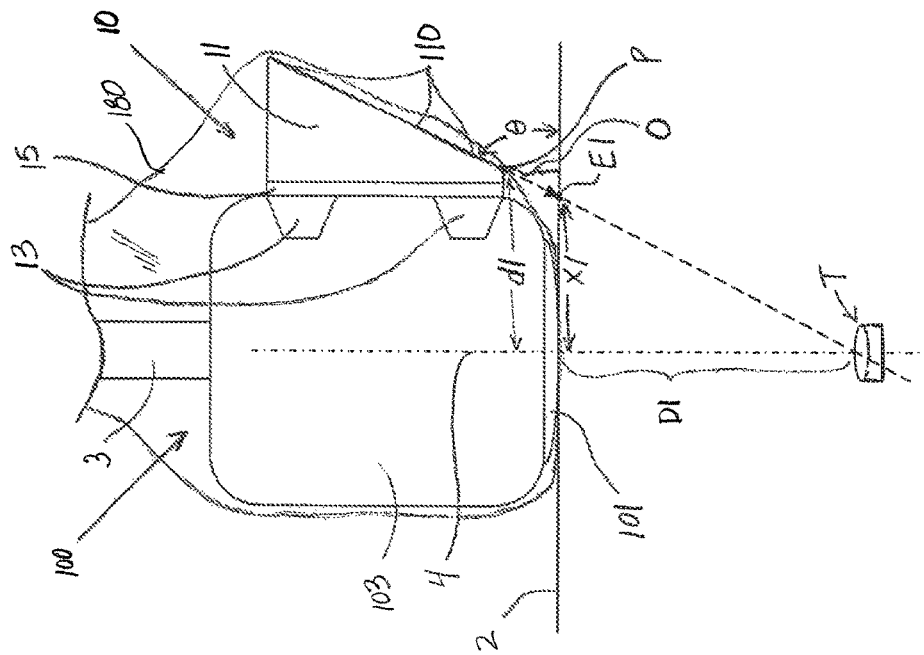

FIGS. 1A-B are schematics depicting a needle guide 10 attached to a medical scanning device 100, for example, a hand-held ultrasound transducer probe, according to some embodiments of the present invention. FIGS. 1A-B illustrate device 100 including a transducer surface 101, to which a plane 2 is approximately tangent at an apex thereof, an external sidewall 103 extending away from transducer surface 101, a longitudinal axis 4 approximately perpendicular to plane 2, and a cord 3 extending from device 100; cord 3 couples the scanning transducer of device 100 to a console (example shown in FIG. 5A), which, for example, controls the transducer function, processes and stores data collected by the transducer, and displays the data. Guide 10 is shown including an indicator element 11, an adjustment mechanism 15 and a joining structure 13, which reversibly attaches guide 10 to device 100 such that indicator element 11 is laterally offset from transducer surface 101 and external sidewall 103. Joining structure 13 may include a pair of spring loaded mounting brackets that may be press fit about external sidewall 103 of device 100.

FIGS. 1A-B further illustrate indicator element 11 including a pointer 110 being formed as a terminating edge of element 11, and adjustment mechanism 15 being coupled to joining structure 13 for moving indicator element 11, with respect to device 100, in a direction approximately parallel to plane 2 without changing an orientation of pointer 110 as defined by an angle θ. According to the illustrated embodiment, angle θ of pointer 110 is predetermined according to an orientation necessary for a percutaneous needle to pass through a subcutaneous target T in order to gain access to an underlying site; according to an exemplary embodiment, for an application described below, in which the percutaneous needle must pass through a foramen of a boney structure, angle θ is between approximately 55 degrees and 65 degrees. With reference to FIGS. 1A-B, it should be appreciated that pointer 110 provides guidance for needle insertion without constraining the needle, so that needle handling on the part of a physician or clinician is not unduly restricted or hampered. According to FIG. 1A, when plane 2 coincides with an epidermis of a body, and scanning device locates subcutaneous target T at a depth D1, indicator element 11 is moved, via adjustment mechanism 15, to locate a terminal end P of pointer 110 at a distance d1 from axis 4 (axis 4 coinciding with target T); distance d1 corresponds to an entry site E1 on the epidermis, to which pointer 110 points by virtue of angle θ, and which entry site E1 is located a distance x1 from axis 4, so that a trajectory of a needle (shown by a dashed line), inserted at E1 per angle θ, passes through target T at depth D1. According to FIG. 1B, when plane 2 coincides with an epidermis of a body, and scanning device locates subcutaneous target T at a depth D2, indicator element 11 is moved, via adjustment mechanism 15, to locate terminal end P of pointer 110 at another distance d2 from axis 4; distance d2 corresponds to another entry site E2 on the epidermis, to which pointer 110 points, and which entry site E2 is located a distance x2 from axis 4, so that a trajectory of a needle (shown by a dashed line), inserted at E2 per angle θ, passes through target T at depth D2. Adjustment mechanism 15 may be any type expanding and collapsing structure (one example being a telescoping structure) for moving indicator element 11, with respect to device 100, along a direction approximately parallel to plane 2, without changing angle θ of pointer 110; and, according to some preferred embodiments, adjustment mechanism 15 is calibrated to move indicator element 11, with respect to device 100, in predetermined increments, each increment corresponding to a different target depth.

With reference to FIGS. 1A-B, it should be appreciated that each of distances x1 and x2 is approximately equal to a tangent of (90°−θ) multiplied by a depth D1, D2, respectively, and that an offset C between terminal end P of pointer 110 and plane 2 is accounted for in the positioning of indicator element 11 at distances d1 and d2, such that pointer 110 points to entry sites E1 and E2 that are located at distances x1 and x2. As offset C) decreases, for example, by enlarging indicator element 11 so that terminal end P of pointer 110 is moved closer to plane 2, distances d1 and d2 approach distances x1 and x2, respectively. According to alternate embodiments of the present invention, guide 10 is either shifted, with respect to device 100, toward plane 2, in its attachment thereto, or indicating element 11 is enlarged (for example, as shown with a dotted line in FIG. 1B), so that terminal end P of pointer 110 is approximately tangent with plane 2 (touching, or close to touching entry sites E1 and E2); for embodiments such as these, offset O is significantly reduced, and distances d1 and d2 become approximately equal to distances x1 and x2, respectively.

Figure 1C:
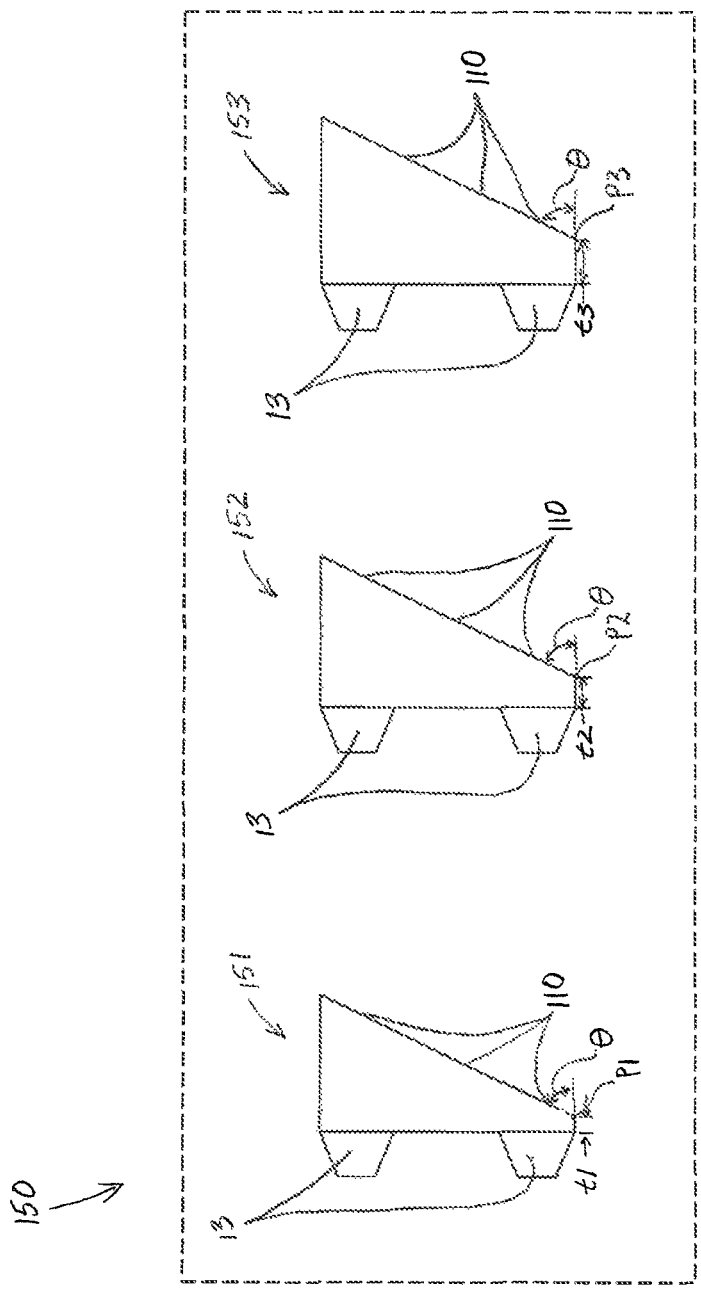
FIG. 1C is a plan view of a needle guide kit, according to some embodiments of the present invention.

It should be noted that a depth of particular subcutaneous targets may not varying significantly, from body to body (patient to patient), such that needle guides, according to alternate embodiments of the present invention, need not include an adjustment mechanism, such as mechanism 15. FIG. 1C is a plan view of a kit 150 including a plurality of needle guides 151, 152, 153, FIG. 1C illustrates each needle guide 151, 152, and 153 having a fixed position, for corresponding terminal ends P1, P2, and P3 of pointers 1110, which are defined by thicknesses t1, t2, t3, respectively. According to the illustrated embodiment, one of guides 151, 152 and 153 may be selected and attached to a scanning device, for example device 100, according to a depth of a target, either foreknown or measured via scanning device 100, that corresponds to the thickness of the selected guide. According to some preferred embodiments, each guide 151, 152, 1153 is labeled to indicate a target depth corresponding to thickness t1, t2, t3, and labeled to direct an attachment thereof, via joining structure 13, in a proper position along sidewall 103 of device 100 so that each pointer 110 points to the needle entry site that corresponds to the depth indicated on the corresponding guide 151, 152, 153. Another embodiment of a "fixed" needle guide will be described below, in conjunction with FIG. 8.

Returning to FIGS. 1A-B, a flexible and transparent disposable covering 180 is shown surrounding device 100 and attached guide 10. A fresh covering 180 placed about device 100 and guide 10, for each successive procedure, protects against contamination between patients when device 100 and guide 10 are reused. Because guide 10 includes pointer 110, which can be easily viewed through cover 180, in order to guide a percutaneous needle insertion, and indicator element 11 may be grasped from outside cover 180 for adjustment via adjustment mechanism 15, there is no need to attach guide 10 outside covering 180; however, according to some embodiments, joining structure 113 fits about device sidewall 103 that is enclosed within covering 180, so that guide 10 may be attached to device 100 outside covering 180. In either situation, inside or outside covering 180, a new guide 10 may be used for each successive procedure, or a same guide 10 may be sterilized and reused in each successive procedure. Disposable embodiments of guide 10 may be inexpensively formed, for example, via injection molding, from a plastic such as ABS or nylon, while reusable embodiments of guide 10 may be formed from a metal or a plastic, such as an acetal resin (i.e. Detring) or a polycarbonate, that can withstand autoclave sterilization temperatures.

FIGS. 2A-B are first and second perspective views of another needle guide 20 attached to medical scanning device 100, according to some alternate embodiments of the present invention. FIG. 2A shows device 100 positioned with transducer surface 101 against plane 2 in an orientation very similar to that shown in FIGS. 1A-B. FIGS. 2A-B illustrate needle guide 20 including a Vixo-part joining structure 231, 232 coupled to an indicator element 21, which is in the form of a plate, and joining structure parts 231, 232 wrapping around external sidewall 103 of device 100 in order to attach guide 20 to device 100 so that indicator element 21 is laterally offset from device transducer surface 101 and external sidewall 103; joining structure parts 231, 232 are shown coupled together via interlocking snap-fit features 23. FIGS. 2A-B further illustrate indicator element 21 including a first pointer 209, a second pointer 210 and a third pointer 211, each extending over a length, along an exposed face of indicator element 21, at a different angle, but each having a common terminal end P20; pointers 209, 210, 211 are shown formed by edges or ledges of increasingly protruding surfaces of the exposed face of element 21, against which a needle may be rested, however pointers 209, 210, 211 may alternately be formed by grooves in the exposed face or any other type of marking on the exposed face that may not provide a support for the needle.

Figure 2C:
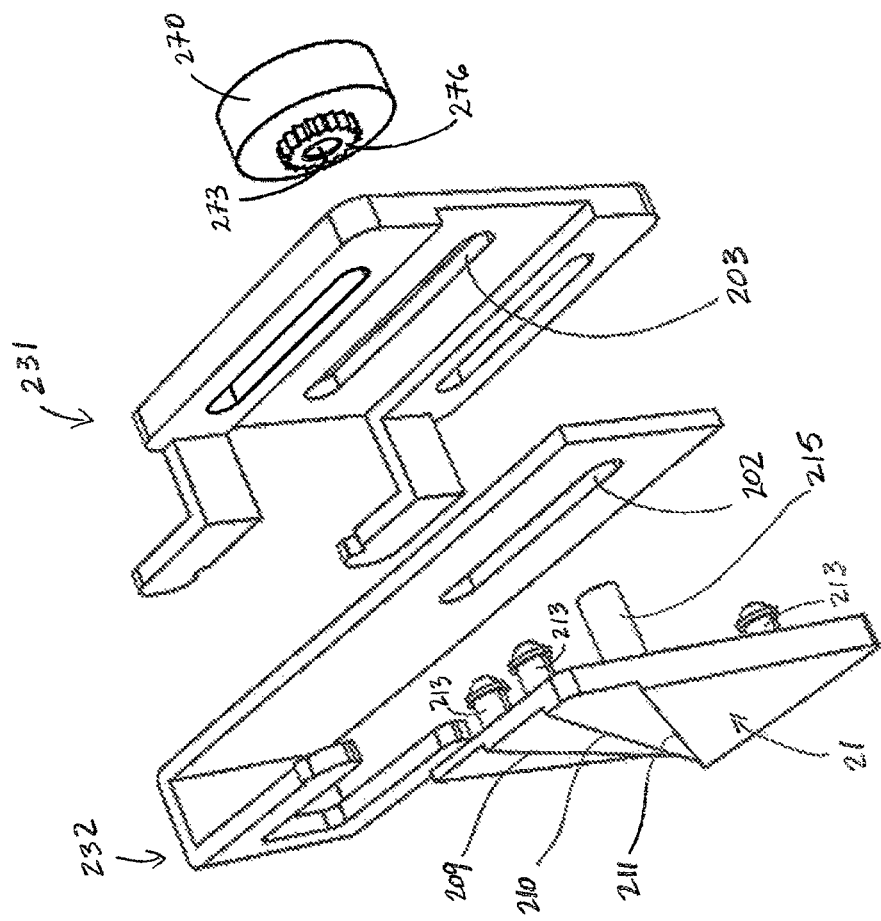
FIG. 2C is an exploded perspective view of the needle guide shown in FIGS. 2A-B, according to some embodiments.

According to the illustrated embodiment, indicator element 21 is coupled to a lateral extension of each of joining structure parts 231 and 232 such that an adjustment mechanism including a knob 270 may move indicator element 21 with respect to device 100, when guide 20 is attached thereto, and with respect to the joining structure. FIG. 2B illustrates indicator element 21 mounted to joining structure part 231 via pegs 213 that extend, from a surface of indicator element 21, which is opposite the exposed face thereof, and through slots 201 of the lateral extension of joining structure part 231; pegs 213 extending in slots 201 maintain a fixed orientation of each pointer 209, 210, 211, while allowing indicator element 21 to be moved toward and away from device 100, in a direction approximately parallel to plane 2, by knob 270 of the adjustment mechanism. Thus, the adjustment mechanism may be used to move terminal end P20 of pointers 209, 210, 211 into a position corresponding to a measured depth of a subcutaneous target, which has been located by device 100, in order to guide insertion of a percutaneous needle along a proper trajectory to pass through the located target, as previously described in conjunction with FIGS. 1A-B. Pointers 209 and 211 on either side of pointer 210 may provide a frame of reference for an acceptable tolerance, for example, approximately ±5 to 10 degrees, on an angle of insertion, as defined by pointer 210, required to pass the needle through a particular subcutaneous target, or pointers 209, 210, 211 may provide guides for alternative angles of entry, each angle of entry appropriate for passage of a needle through a different type of subcutaneous target. It should be noted that although FIG. 2A shows the three pointers 209, 210, 211, alternate embodiments of guide 20 may include just one pointer, or any number of pointers. Referring now to FIG. 2C, which is an exploded perspective view of needle guide 20, in conjunction with FIG. 2B, the adjustment mechanism of guide 20 will be described in greater detail. FIGS. 2B-C illustrate the adjustment mechanism including knob 270, a rack 260 coupled to joining structure part 231, and a pinion element 276 coupled to knob 270 and including a bore 273 to receive a shaft 215 extending from the surface of indicator element 21 opposite the exposed face thereof. According to the illustrated embodiment, shaft 215 of indicator element 21 extends through a slot 202 of joining structure part 232 and through a slot 203 of joining structure part 231 to mate with bore 273 of pinion element 276; when knob 270 is rotated, pinion element 276 rotates about shaft 215 and travels along rack 260 thereby moving indicator element 21 in the direction parallel to plane 2. FIG. 2B illustrates calibration markings 275 located both on knob 270 and above rack 260 so that a position of knob 270 with respect to rack 260 may be correlated by a user to a depth of the target beneath device 100 and located by device 100, which depth may have been measured by device 100. According to an alternate embodiment, rather than the illustrated rack-and-pinion interface, slot 202 and/or slot 203 includes a series of detents, or recesses, spaced apart along a length thereof and into which shaft 213 of indicator element 21 may be positioned by sliding shaft 213, with or without knob 270, along the length.

Joining structure parts 231, 232, indicator element 21, and the adjustment mechanism components described above may all be formed, for example, via injection molding, from a suitable plastic, for example, ABS, nylon, acetal resin, or polycarbonate, and then snap fitted together to assembly guide 20. Both device 100 and attached guide 20 may be inserted into a transparent and flexible protective covering, for example, similar to covering 180 shown M FIGS. 1A-B, for performing a scan and an associated needle insertion, since pointers 209, 210, 211 of guide 20, similar to guide 10, can easily be viewed through the covering, to guide the orientation of a needle to an indicated entry site, and the adjustment mechanism of guide 20 may be manipulated by grasping knob 270 from outside the covering. Alternately, joining structure parts 231, 232 of guide 20 may be snapped together around device 100 which has already been inserted into the protective covering so that guide is outside the covering during the scanning and needle insertion.

FIG. 3A is a perspective view of a needle guide 30 attached to medical scanning device 100, according to additional embodiments of the present invention; and FIG. 3B is a top perspective view of needle guide 30. FIGS. 3A-B illustrate a joining structure 33 of guide 30 including a sidewall having portions 331, 332, 333 and 334 to form a receptacle 335 for holding device 100; receptacle 335 includes a first opening 313, through which device 100 is inserted, and a second opening 315, through which transducer surface 101 of device 100 is exposed for scanning, and joining structure 33 includes a spring member 360, which may help to position and to retain device 100 within receptacle 335. An operator may position device 100 within receptacle 335 such that transducer surface 101 protrudes slightly from second opening 315, as shown, or such that transducer surface 101 is approximately flush with a flange 340 of joining structure 33; flange 340 is shown extending outward from the joining structure sidewall, approximately aligned with opening 315, and may serve to maintain a constant orientation of device 100 when transducer surface 101 is placed over an epidermis during scanning and needle insertion.

FIGS. 3A-B further illustrate an indicator element 31 of guide 30 including a pointer 310, formed by a groove in a side surface thereof; indicator element 31 is shown coupled to flange 340 of joining structure 33 via a coupling 312, into which indicator element 31 is snap-fitted at a fixed angle with respect to joining structure 33; according to some embodiments coupling 312 allows indicator element to pivot, per arrow A, into various fixed positions, for example in 10 degree increments. According to the illustrated embodiment, a position of a terminal end P30 of pointer 310 is fixed in relation to joining structure 33, and an adjustment mechanism of guide 30 includes a knob 354 to move joining structure 33, with respect to device 100, in a direction parallel to a plane (like plane 2 shown in FIGS. 11A-B and FIG. 2A), which is approximately tangent with an apex of transducer surface 101 and approximately perpendicular to longitudinal axis 4 of device 100, thereby moving indicator element 31 with respect to device 100 in a direction parallel to the same plane. It should be noted that pointer 310 may alternately be formed by an edge protruding from the side surface of indicator element 31 or just as the side surface itself.

FIG. 3B illustrates the adjusting mechanism of guide 30 including a knob 354, located adjacent an external surface of sidewall portion 332, and a shaft 352 extending from knob 354 through sidewall portion 332 to a terminal end 305 thereof, which contacts inserted device 100 (device 100 represented with a dashed line in FIG. 3B), and forces device 100 against spring member 360. Knob 354 may be used to advance or retract terminal end 305 of shaft 352, per arrow B, causing a relative movement between device 100 and both joining structure 33 and indicator element 31, so that indicator element 31 remains in a fixed location with respect to joining structure 33 while being moved with respect to device 100. Although spring member 360 is shown as a leaf spring, it should be appreciated that any type of spring member, which applies a resistive force against device sidewall 103 to hold device 100 in receptacle while allowing movement of device 100 therein, may be incorporated by embodiments of the present invention.

Referring back to FIG. 3A, knob 354 is shown including calibration marks 375 to be used in conjunction with an indicator 385, which is coupled to sidewall portion 332, in proximity to knob 354. With reference to FIGS. 3A-B it should be appreciated that a threaded interface between shaft 352 and sidewall portion 332 controls travel, per arrow B, of terminal end 305; the controlled travel of terminal end 305, which is effected by rotating knob 354, is calibrated to position device 100 with respect to indicator element 31, such that indicator marks 375, being aligned with indicator 385, each correspond to a different depth of a subcutaneous target, located by device 100, that a needle will pass through being guided by pointer terminal end P30, which is located at a distance d from axis 4 of device 100, and according to the angular orientation of pointer 310. According to some alternate embodiments, shaft 352 includes detent notches interfacing with sidewall portion 332, rather than threads, and knob 354 is pushed rather than turned in order to adjust distance d.

Figure 4B:
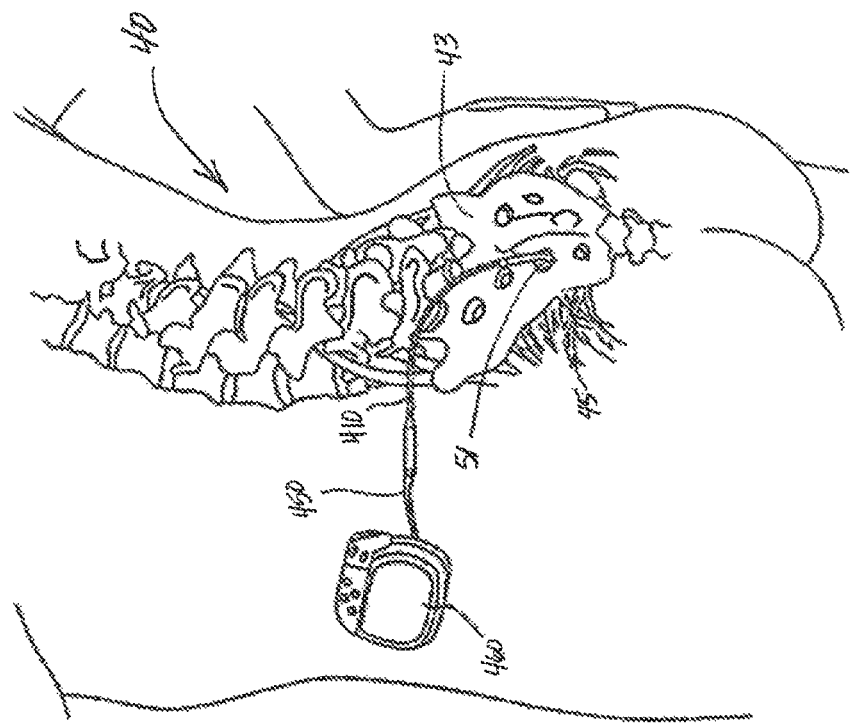
FIGS. 4A-B are schematics depicting an exemplary procedure that may employ embodiments of the present invention.
Figure 4A:
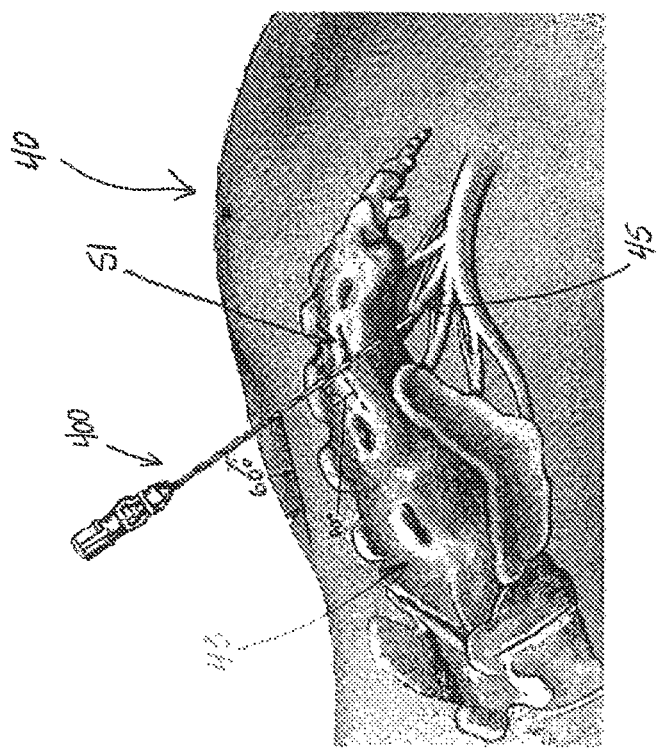

FIGS. 4A-B are schematics depicting an exemplary procedure that may employ embodiments of the present invention. FIG. 4A illustrates sacral nerves 45 of a patient 40 located adjacent to an anterior surface of the patient's sacrum 43, which is the relatively large triangular bone situated at the lower part of the vertebral column. FIG. 4A further illustrates access to nerves 45 being gained by a percutaneous needle 400 inserted, from a posterior side of sacrum 43, through a foramen 51 of sacrum 43 (typically, the third sacral foramen, or S3). Such access is desired in order to provide electrical stimulation, or neuromodulation treatment, to sacral nerves 45, thereby influencing the behavior of the patient's organs that sacral nerves 45 innervate, for example, to treat urinary incontinence. FIG. 4B illustrates an implanted neuromodulation system including a stimulation device 460 coupled to an elongate medical electrical lead 410 via an extension lead 450; prior to coupling with device 460, lead 410 has been inserted through sacral foramen 51, for example, via needle 400, and an electrode of lead 410 has been coupled to underlying sacral nerve 45 in order to deliver controlled electrical stimulation thereto from device 460.

With reference back to FIG. 4A, it may be appreciated that protuberances of sacrum 43 can provide landmarks for determining an appropriate entry site for needle 400, and knowledge of a typical curvature of sacrum 43, in relation to a contour of the exterior body surface, or epidermis of patient 40, surrounding the needle entry site, has helped to establish an approximately 60 degree angle of insertion for needle 400, which allows needle 400 to pass through foramen 51 in order to contact nerves 45, and which angle is known to those skilled in the art. Once properly inserted, as illustrated in FIG. 4A, needle 400 provides a pathway, through a lumen thereof, by which lead 410 may be implanted as an initial step in the implantation of the system shown in FIG. 4B.

Often times the needle insertion illustrated in FIG. 4A is accomplished under local anesthetic by probing with needle 400 and using tactile feedback to find foramen 51. For a skilled and experience physician, or clinician, such an approach may be acceptable, but, with the advent of non-invasive medical scanning systems, for example, those including handheld ultrasound transducer probes, an approach that employs these systems, to provide more concrete feedback in guiding needle insertion, may be preferred in many instances.

Figure 5A:
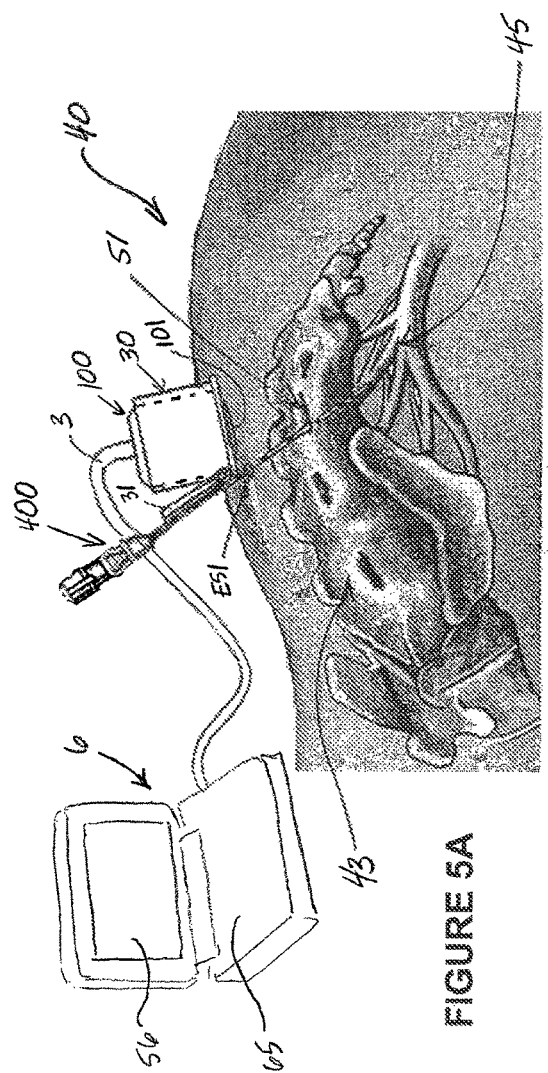
FIG. 5A is a schematic depicting percutaneous needle access obtained according to some methods of the present invention.
Figure 5B:
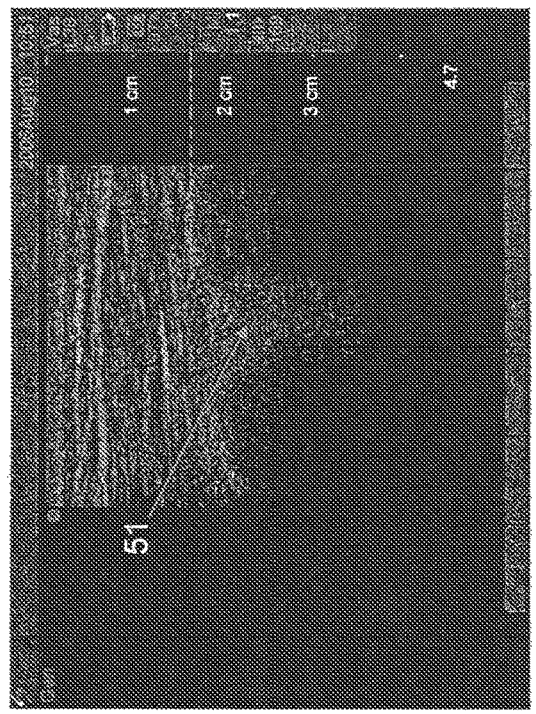
FIG. 5B is a reproduction of an exemplary ultrasound scan showing a sacral foramen.

FIG. 5A is a schematic depicting percutaneous needle access obtained according to some methods of the present invention, wherein device 100 and needle guide 30 are employed; and FIG. 5B is a reproduction of an exemplary ultrasound scan obtained by device 100 in locating sacral foramen 51. FIG. 5A illustrates transducer surface 101 of device 100 placed over the epidermis of patient 40 and device 100 coupled via cord 3 to a console 6; according to exemplary embodiments of the present invention, device 100 and console 6 make up an ultrasound machine wherein device 100 is an ultrasound transducer probe that sends and receives sound waves, and console 6 includes a central processing unit, transducer pulse controls, a display screen 56 and a user interface 65, for example a key board and/or touch pad. According to the illustrated embodiment, a physician or clinician has placed transducer surface 101 of device 100 over the epidermis of patient 40, which overlies sacrum 43, and has located foramen 51 by moving transducer surface 101 along sacrum 43 while scanning. Guide 30 may have been attached to device either before or after scanning to locate foramen 51. Although not shown, those skilled in the art will appreciate that device 100 and, optionally, guide 30 too, if attached prior to scanning, will typically be placed within a protective covering, for example, like cover 180 previously described, and that a conductive gel will be spread between transducer surface 101 and the covering to facilitate the scanning process. FIG. 5B shows an image 560, which may be generated by device 100, once foramen 51 has been located by device 100, and displayed on screen 56; image 560 was obtained with a 38 mm broadband linear array ultrasound transducer probe of MicroMaxx® system, available from SonoSite, Inc., using a scanning frequency of 7.5 MHz.

With further reference to FIG. 5B, those skilled in the art will appreciate that a difference in reflection of ultrasound energy from bone and adjacent soft tissue creates the contrast between bone (shown black in image 560) and soft tissue (shown gray in image 560) that helps to identify the location of foramen 51. In addition to locating foramen 51, device 100 in conjunction with image 560 may be used to determine a depth of the posterior opening of foramen 51; depths are shown by tick marks along the right hand side of image 560, and a dashed white line has been superimposed on the image to indicate an approximate depth between 1.5 and 2 cm of the posterior opening of foramen 51, as measured by the ultrasound probe in this particular instance. The depth of the opening may vary from patient to patient depending upon a thickness of subcutaneous tissue overlying the sacrum for each patient. As previously described, indicator element 31 is moved with respect to device 100, in the previously described parallel direction, into a position where pointer 310 of indicator element 31 points to an appropriate needle entry site E51 that corresponds to the fixed angular orientation of indicator element 31 (FIG. 5A). With reference back to FIG. 4A, the fixed angular orientation of indicator element 31 should be approximately 60 degrees to assure passage of needle 400 through foramen 51 to underlying nerves 45; however, it should be understood that needle guides of the present invention may be used for other applications wherein other angular orientations are appropriate. It should be noted that any of the previously described embodiments of needle guides, for example, guides 10 and 20, may be employed for guiding needle 400.

Figure 6A:
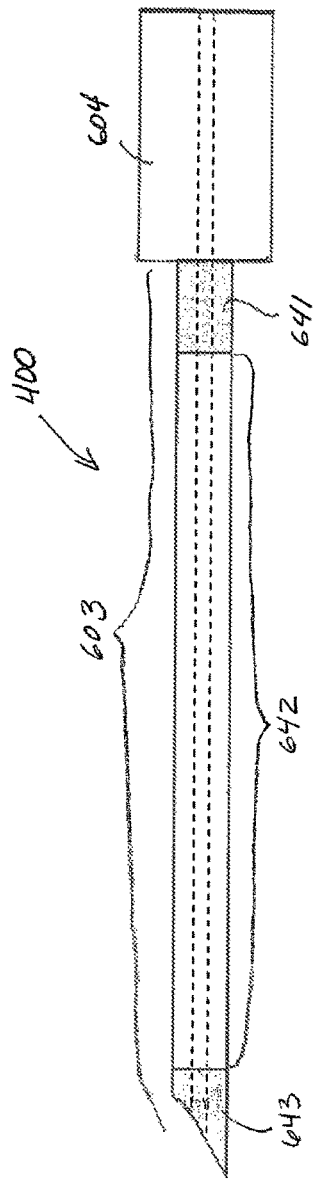
FIG. 6A is a plan view of a percutaneous access needle.
Figure 6B:
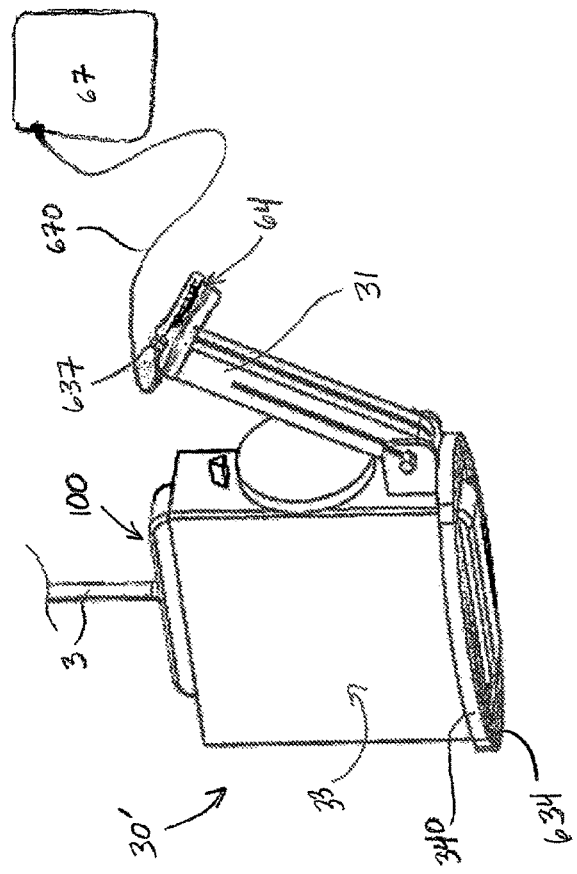
FIG. 6B is a perspective view of an alternate embodiment of the guide shown in FIGS. 3A-B.

Once foramen 51 has been located, a depth thereof measured, and, if necessary, guide 30 has been adjusted, needle 400 may be inserted at the entry site, and per the orientation indicated by indicator element 31. According to some methods of the present invention, the insertion of needle 400 may be visualized via ultrasound, for example, on display screen 56 (FIG. 5A); a metal shaft of needle 400 will be echogenic for ultrasound visualization, and some embodiments of needle 400 may have a roughened surface known to enhance echogenic properties. Alternately, or additionally, proper insertion of needle 400 may be verified via electrical testing. Turning now to FIG. 6A, which is a plan view of percutaneous access needle 400, needle 400 is shown including a conductive shaft 603 attached to a hub 604, wherein a tip 643 and a proximal portion 641 of shaft 603 are exposed for electrical contact, and a length 642 of shaft 603, between tip 643 and proximal portion 641 is insulated. According to the illustrated embodiment, once needle 400 is passed through foramen 51, a test stimulation may be applied at portion 641 in order to determine if tip 643 is contacting nerve 45; if contact with nerve 45 is made a motor response in the buttock area will be observed. FIG. 6B is a perspective view of an alternate embodiment of guide 30, denoted as guide 30', which includes electrical contact features to facilitate application of the test stimulation to needle 400.

FIG. 6B illustrates indicator element 31 of guide 30' including a mounting feature 637 for an electrical contact clip 64, which is shown coupled via lead wire 670 to a test stimulator device 67; contact clip 64, being mounted to guide 30', as shown, may provide stability to inserted needle 400, being coupled to clip 64 during the stimulation testing. According to the illustrated embodiment, mounting feature 637 is formed by a post, which protrudes from an end of indicator element 31 and about which clip 64 may be attached for mounting; if a protective covering is disposed about device 100 and guide 30', clip 64 may still be mounted on feature 637 from outside the covering. Although not shown, it should be appreciated that a circuit for test stimulation must be completed by grounding stimulator device 67; such grounding is typically accomplished via a ground pad connected to the epidermis of the patient. However, FIG. 6B further illustrates a conductive surface 634, which is coupled to flange 340 of guide 30 and is electrically isolated from mounted contact clip 64, and which may be used to ground stimulator device 67. According to the illustrated embodiment, when guide 30' is attached to device 100, and transducer surface 101 is placed over the epidermis for scanning, a ground wire (not shown) of stimulator device 67 may be coupled to conductive surface 634 of guide 30', which is grounded to the epidermis, for example, via direct contact therewith and/or via an interface of conductive gel. Thus, guide 30' includes useful features facilitating handling of inserted needle 400 in conjunction with device 100 during electrical stimulation testing for verification of proper needle insertion. It should be noted that alternate embodiments of guide 30' need not include both mounting feature 637 and conductive surface 634, but may include one or the other.

Figure 7:
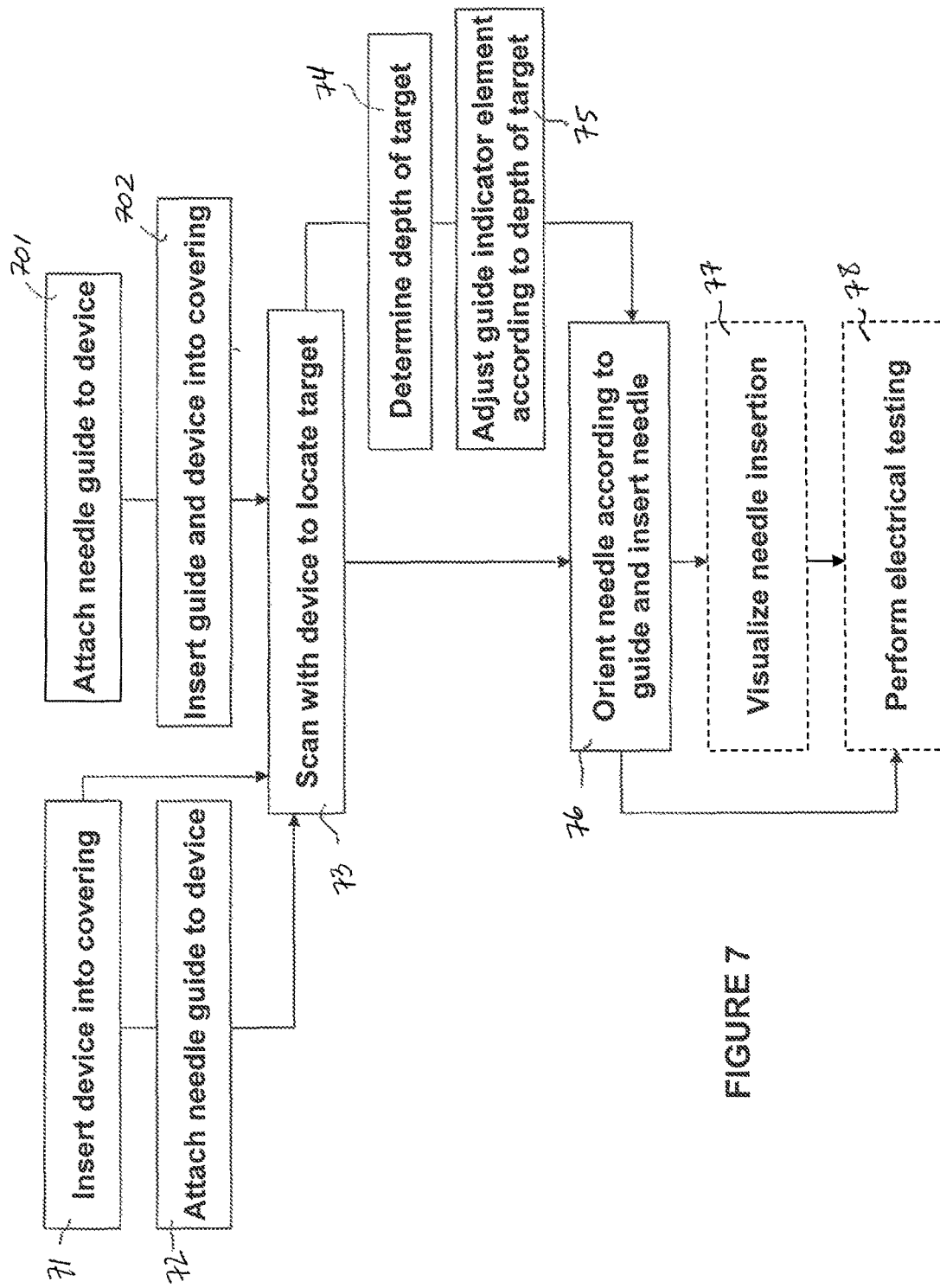
FIG. 7 is a flow chart outlining various methods of the present invention.

FIG. 7 is a flow chart outlining/summarizing various methods of the present invention, which have been discussed in greater detail above. FIG. 7 illustrates alternative pairs of initial steps: steps 71 and 72 wherein a medical scanning device (i.e. device 100) is inserted into a protective covering prior to attaching a needle guide (i.e. guide 10, 20, or 30) thereto; and steps 701 and 702 wherein the needle guide is attached to the device and then the device and attached guide inserted into the protective covering. FIG. 7 shows, following either of these pair of initial steps, a step 73, wherein scanning is performed to locate a target (i.e. foramen 51); however, it should be noted that step 73 may be performed in between steps 71 and 72, according to an alternate method, such that scanning is performed to locate the target before the needle guide is attached to the device. After step 73, a depth of the located target is determined, per step 74, and then the guide is adjusted according to the depth, per step 75, so that a needle (i.e. needle 400) may be oriented and inserted into an entry site E51) indicated by the adjusted needle guide, per step 76; of course, if an initial position of an indicator element of the guide happens to coincide with the determined depth of the target, adjustment of the guide, per step 75, is not necessary. According to some alternate methods, step 76 immediately precedes step 73, wherein the depth of the located target is foreknown and the needle guide need not be adjusted; an embodiment of a fixed needle guide, that does not include an adjustment mechanism, was described in conjunction with FIG. 1C, and another embodiment will be described below in conjunction with FIG. 8. FIG. 7 further illustrates optional steps 77 and 78 following insertion of the needle, per step 76: according to step 77, the needle is visualized during insertion, and, according to step 78, electrical testing is performed to verify proper insertion of the needle. It should be noted that either of steps 77 and 78 may be included in a method without the other being included.

Figure 8:
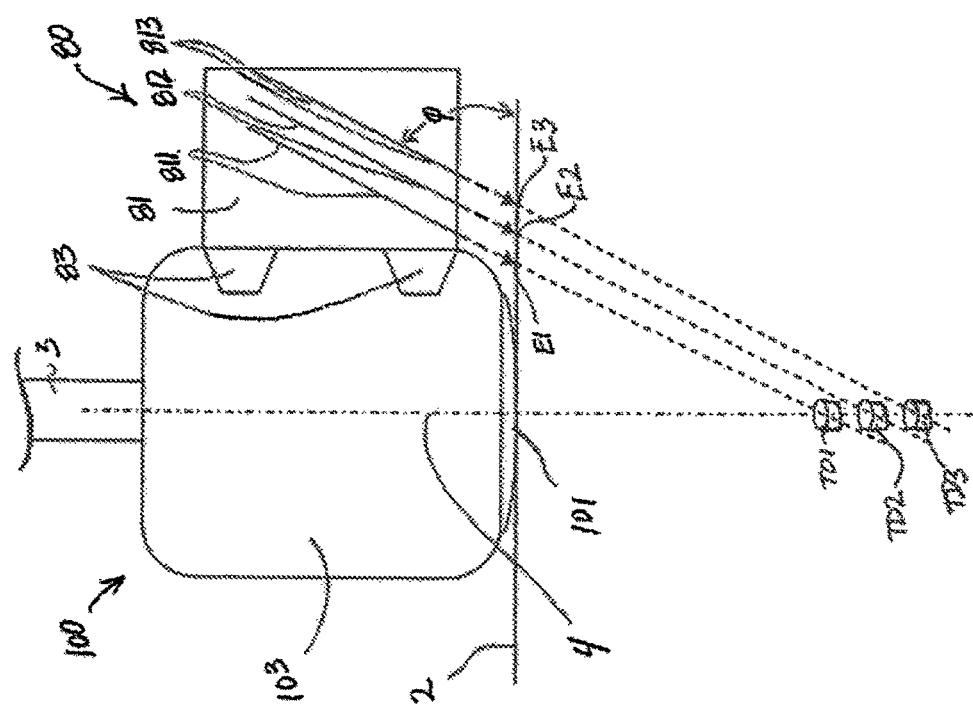
FIG. 8 is a schematic depicting a fixed needle guide, attached to a medical scanning device, according to further alternate embodiments of the present invention.

Various embodiments of adjustable needle guides have been heretofore described, along with one embodiment of a fixed needle guide; now, another embodiment of a fixed needle guide will be described in conjunction with FIG. 8. FIG. 8 is a schematic depicting a fixed needle guide 80, attached to medical scanning device 100, wherein plane 2 is approximately tangent to the apex of transducer surface 101 and approximately perpendicular to longitudinal axis 4 of device 100. FIG. 8 illustrates guide 80 including a plate 81 and a joining structure 83, which reversibly attaches guide 80 to device 100 such that plate 81 extends laterally from transducer surface 101 and external sidewall 103 of device 100. FIG. 8 further illustrates plate 81 including pointers 811, 812, 813, which extend over a length along an exposed surface of plate 81; pointers 811, 812, 813 may be formed as grooves or protruding surfaces, or any other type of marking on the exposed surface of plate 81. According to the illustrated embodiment, each of pointers 811, 812, 813 extend at a fixed angle (p with respect to plane 2, and are space apart from one another in a direction approximately parallel with plane 2; each of pointers 811, 812, 813 points to a needle entry site E1, E2, E3, respectively, each of which corresponds to a depth of a target TD1, TD2, TD3, respectively, and depending on which depth is measured for the target, the corresponding pointer is selected to guide insertion of a percutaneous needle per the corresponding insertion path shown with dashed lines. Each of pointers 811, 812, and 813 may include a visible calibration mark indicating the depth to which each correspond, or some kind of color coding identifying the corresponding depth. Although not shown, it may be appreciated that both device 100 and attached guide 80 may be enclosed in a translucent protective covering, for example, similar to that shown in FIGS. 1A-B, for scanning and subsequent guiding of a percutaneous needle insertion according to the selected pointer, since pointers 811, 812, 813, may be visualized through the covering.

In the foregoing detailed description, the invention has been described with reference to specific embodiments. However, it may be appreciated that various modifications and changes can be made without departing from the scope of the invention as set forth in the appended claims.

The invention claimed is:

1. A method for gaining percutaneous access through a sacral foramen for stimulation of a sacral nerve, the method comprising:
   attaching a percutaneous needle guide to a medical scanning device such that an indicator element of the guide is laterally offset from a transducer surface of the device, wherein the indicator element has an exposed face;
   placing the transducer surface of the device over an epidermis of a body;
   moving the device over the epidermis, while scanning with the device, to locate the sacral foramen;
   orienting a percutaneous needle toward a needle entry site on the epidermis, the needle entry site being indicated by a chosen pointer that is one of a plurality of pointers on the exposed face of the indicator element of the guide where the plurality of pointers comprise only two surfaces of the indicator element for each pointer, where a first surface of the two surfaces provides a plane that is perpendicular to the plane provided by a second surface of the two, and the needle being oriented according to an entry angle depicted by the pointer, wherein orienting the percutaneous needle further comprises moving the indicator element by rotating a knob of an adjustment mechanism that is directly coupled to a pinion where the knob and pinion are rotationally coupled to the indicator element with the pinion rotating against a rack mounted to the needle guide separately from the indicator element to move the indicator element relative to the rack to one of a plurality of positions without changing an angular orientation of any of the plurality of pointers; and
   inserting the oriented percutaneous needle into the entry site and through the sacral foramen;
   wherein the orienting and inserting of the needle are performed without the needle being constrained by the chosen pointer in a direction perpendicular to a direction of insertion of the needle.

2. The method of claim 1, further comprising inserting the device and the attached guide into a covering before moving the device over the epidermis.

3. The method of claim 1, wherein the guide is attached to the device after moving the device to locate the sacral foramen.

4. The method of claim 1, further comprising:
   determining a depth of the sacral foramen from a scan of the device located over the sacral foramen; and
   wherein orienting the percutaneous needle further comprises moving, with respect to the device, in a direction approximately parallel to a plane that is approximately tangent with an apex of the transducer surface of the device and approximately perpendicular to a longitudinal axis of the device, the indicator element of the attached guide from a first position to a second position, the second position corresponding to the determined depth of the sacral foramen and the entry angle depicted by the chosen pointer.

5. The method of claim 4, wherein the device is held over the sacral foramen when the indicator element is moved.

6. The method of claim 4, wherein the guide includes a joining structure and wherein:
   attaching the guide to the device comprises inserting the device into a receptacle of the guide, the receptacle being formed by a sidewall of the joining structure such that the transducer surface of the inserted device is exposed for scanning through an opening in the sidewall of the joining structure, and a spring member of the guide, which is mounted against a portion of the joining structure, interfaces with an external sidewall of the inserted device; and
   moving the indicator element from the first position to the second position comprises adjusting the knob of the adjustment mechanism of the guide to move the joining structure of the guide with respect to the device, against a resistive force of the spring member, the adjustment mechanism being coupled to the joining structure and extending through the sidewall of the joining structure to contact the external sidewall of the inserted device, opposite the interface with the spring member.

7. The method of claim 1, further comprising visualizing insertion of the needle via the device.

8. The method of claim 1, further comprising coupling a stimulation source to the needle for electrical testing.

9. The method of claim 8, further comprising coupling the stimulation source to the guide for grounding via an electrical coupling between the guide and the epidermis.

10. The method of claim 1, wherein each pointer of the plurality of pointers is formed in an exposed surface of a plate of the indicator, each of the plurality of pointers extending at a fixed angle with respect to a plane that is approximately tangent with an apex of the transducer surface of the device; and further comprising:
    determining a depth of the sacral foramen from a scan of the device located over the sacral foramen; and
    wherein orienting the percutaneous needle further comprises moving, with respect to the device, in a direction approximately parallel to the plane that is approximately tangent with the apex of the transducer surface and approximately perpendicular to a longitudinal axis of the device, the indicator element of the attached guide from a first position to a second position, without changing an angular orientation of any of the plurality of pointers, the second position corresponding to the determined depth of the sacral foramen and the entry angle depicted by the chosen pointer.

11. A method for gaining percutaneous access through a sacral foramen for stimulation of a sacral nerve, the method comprising:
    attaching a percutaneous needle guide to a medical scanning device such that an indicator element of the guide is laterally offset from a transducer surface of the device, wherein the indicator element has an exposed face;
    placing the transducer surface of the device over an epidermis of a body;
    moving the device over the epidermis, while scanning with the device, to locate the sacral foramen;
    orienting a percutaneous needle toward a needle entry site on the epidermis, the needle entry site being indicated by a pointer on the exposed face of the indicator element of the guide, and the needle being oriented according to an entry angle depicted by the pointer;
    inserting the oriented percutaneous needle into the entry site and through the sacral foramen;
    wherein the orienting and inserting of the needle are performed without the needle being constrained by the pointer;

determining a depth of the sacral foramen from a scan of the device located over the sacral foramen;

moving, with respect to the device, in a direction approximately parallel to a plane that is approximately tangent with an apex of the transducer surface of the device and approximately perpendicular to a longitudinal axis of the device, the indicator element of the attached guide from a first position to a second position, the second position corresponding to the determined depth of the sacral foramen and the entry angle depicted by the pointer;

wherein the guide includes a joining structure and wherein:

attaching the guide to the device comprises inserting the device into a receptacle of the guide, the receptacle being formed by a sidewall of the joining structure such that the transducer surface of the inserted device is exposed for scanning through an opening in the sidewall of the joining structure, and a spring member of the guide, which is mounted against a portion of the joining structure, interfaces with an external sidewall of the inserted device; and moving the indicator element from the first position to the second position comprises adjusting a knob of an adjustment mechanism of the guide to move the joining structure of the guide with respect to the device, against a resistive force of the spring member, the adjustment mechanism being coupled to the joining structure and extending through the sidewall of the joining structure to contact the external sidewall of the inserted device, opposite the interface with the spring member.

12. A method for gaining percutaneous access through a sacral foramen for stimulation of a sacral nerve, the method comprising:

attaching a percutaneous needle guide to a medical scanning device such that an indicator element of the guide is laterally offset from a transducer surface of the device, wherein the indicator element has an exposed face;

placing the transducer surface of the device over an epidermis of a body;

moving the device over the epidermis, while scanning with the device, to locate the sacral foramen;

orienting a percutaneous needle toward a needle entry site on the epidermis, the needle entry site being indicated by a chosen pointer that is one of a plurality of pointers on the exposed face of the indicator element of the guide where each pointer of the plurality of pointers comprises a separate edge of increasingly protruding surfaces of an exposed face of the indicator element, and the needle being oriented according to an entry angle depicted by the pointer, wherein orienting the percutaneous needle further comprises moving the indicator element by rotating a knob directly coupled to a pinion where the knob and pinion are rotationally coupled to the indicator element with the pinion rotating against a rack mounted to the needle guide separately from the indicator element to move the indicator element relative to the rack to one of a plurality of positions without changing an angular orientation of any of the plurality of pointers; and inserting the oriented percutaneous needle into the entry site and through the sacral foramen;

wherein the orienting and inserting of the needle are performed without the needle being constrained by the chosen pointer in a direction perpendicular to a direction of insertion of the needle.

13. A method for gaining percutaneous access through a sacral foramen for stimulation of a sacral nerve, the method comprising:

attaching a percutaneous needle guide to a medical scanning device such that an indicator element of the guide is laterally offset from a transducer surface of the device, wherein the indicator element has an exposed face;

placing the transducer surface of the device over an epidermis of a body;

moving the device over the epidermis, while scanning with the device, to locate the sacral foramen;

orienting a percutaneous needle toward a needle entry site on the epidermis, the needle entry site being indicated by a chosen pointer that is one of a plurality of pointers on the exposed face of the indicator element of the guide where the plurality of pointers comprise only two surfaces of the indicator element for each pointer, where a first surface of the two surfaces provides a plane that is perpendicular to the plane provided by a second surface of the two, and the needle being oriented according to an entry angle depicted by the pointer, wherein orienting the percutaneous needle further comprises moving the indicator element by rotating a pinion that is rotationally coupled to the indicator element with the pinion rotating against a rack mounted to the needle guide separately from the indicator element to move the indicator element relative to the rack to one of a plurality of positions without changing an angular orientation of any of the plurality of pointers; and inserting the oriented percutaneous needle into the entry site and through the sacral foramen;

wherein the orienting and inserting of the needle are performed without the needle being constrained by the chosen pointer in a direction perpendicular to a direction of insertion of the needle.

* * * * *